(12) United States Patent
Patel et al.

(10) Patent No.: US 7,411,087 B2
(45) Date of Patent: Aug. 12, 2008

(54) PROCESS FOR PREPARATION OF BISPHOSPHONIC ACID COMPOUNDS

(75) Inventors: Vijaykumar Muljibhai Patel, Akota (IN); Trinadha Rao Chitturi, Akota (IN); Rajamannar Thennati, Akota (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 10/569,308

(22) PCT Filed: Aug. 10, 2004

(86) PCT No.: PCT/IN2004/000238

§ 371 (c)(1),
(2), (4) Date: Feb. 21, 2006

(87) PCT Pub. No.: WO2005/044831

PCT Pub. Date: May 19, 2005

(65) Prior Publication Data

US 2006/0293524 A1    Dec. 28, 2006

(30) Foreign Application Priority Data

Aug. 21, 2003 (IN) .................. 837/MUM/2003

(51) Int. Cl.
*C07F 9/22* (2006.01)
*C07F 9/28* (2006.01)

(52) U.S. Cl. ........................ 562/13; 546/22; 546/23; 548/119

(58) Field of Classification Search ............... 562/13; 546/22, 23; 548/119
See application file for complete search history.

(56) References Cited

U.S. PATENT DOCUMENTS

| 4,304,734 A | * | 12/1981 | Jary et al. | ............ 562/13 |
| 4,407,761 A | * | 10/1983 | Blum et al. | ............ 562/13 |
| 4,705,651 A | | 11/1987 | Staibano | |
| 4,922,007 A | | 5/1990 | Kieczykowski et al. | |
| 4,942,157 A | * | 7/1990 | Gall et al. | ............ 514/108 |
| 5,002,937 A | * | 3/1991 | Bosies et al. | ............ 514/108 |
| 5,019,651 A | | 5/1991 | Kieczykowski | |
| 5,908,959 A | | 6/1999 | Kubela et al. | |
| 2003/0013918 A1 | | 1/2003 | Cowan et al. | |
| 2004/0043967 A1 | | 3/2004 | Lidor-Hadas et al. | |

FOREIGN PATENT DOCUMENTS

| EP | 0 462 663 B1 | 9/1995 |
| EP | 0 402 152 B1 | 11/1995 |
| WO | 01/57052 A1 | 8/2001 |
| WO | 02/090367 A1 | 11/2002 |
| WO | WO 02/090367 A1 | 11/2002 |

\* cited by examiner

*Primary Examiner*—Peter G O'Sullivan
(74) *Attorney, Agent, or Firm*—Merchant & Gould P.C.

(57) ABSTRACT

The present invention provides a novel process for preparation of bisphosphonic acids or salts thereof, e.g. alendronic acid, by reacting a carboxylic acid, phosphorous acid and a halophosphorous compound in a water miscible neutral solvent.

14 Claims, No Drawings

PROCESS FOR PREPARATION OF BISPHOSPHONIC ACID COMPOUNDS

The present invention relates to an improved process for preparation of bisphosphonic acid compounds, represented by a compound of formula 1 or salts thereof. More specifically the present invention relates to a process for preparation of compound of formula 1 or a salt thereof by reaction of a carboxylic acid compound of formula 2 or a salt thereof with a mixture of phosphorous acid and phosphorous trichloride ($PCl_3$) in sulfolane.

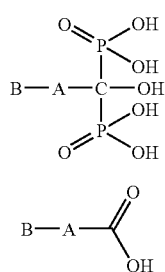

Formula 1

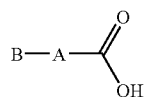

Formula 2

The present invention particularly relates to a process for the preparation of bisphosphonic acid compounds of formulae 3 to 10, namely, alendronic acid, pamidronic acid, risedronic acid, zoledronic acid, ibandronic acid, minodronic acid, neridronic acid and olpadronic acid, respectively or salts thereof.

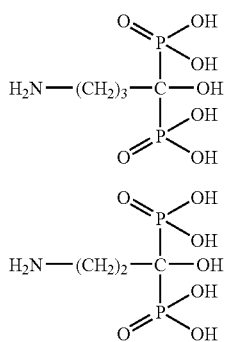

Formula 3

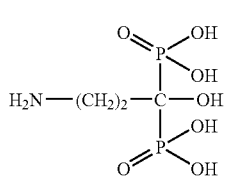

Formula 4

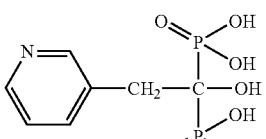

Formula 5

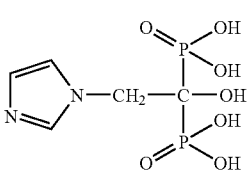

Formula 6

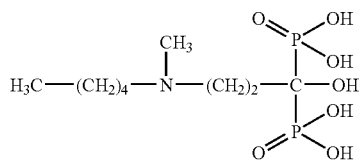

Formula 7

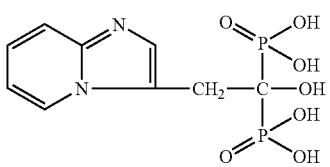

Formula 8

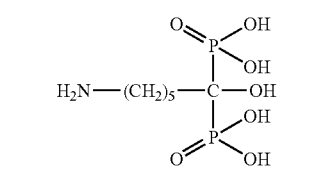

Formula 9

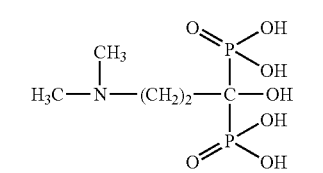

Formula 10

Bisphosphonate compounds have generally been prepared by the reaction of carbonyl compounds with phosphorous halides. 4-Amino-1-hydroxybutylidene-1,1-bisphosphonic acid (alendronic acid, a compound of formula 3) or salts thereof are prepared by the reaction of 4-aminobutyric acid with a mixture of phosphorous acid and one of the three phosphorous chlorides; viz. phosphorous trichloride ($PCl_3$), phosphorous oxychloride ($POCl_3$) or phosphorous pentachloride ($PCl_5$), then quenching the reaction mixture with water followed by heating to hydrolyze the phosphorous intermediates.

Different processes using a variety of different solvents/carriers have been reported in the literature for making the reaction mixture homogenous for preparation of bisphosphonates, however they have some disadvantages associated with their use.

U.S. Pat. No. 4,407,761 (referred to herein as the '761 patent) teaches preparation of 4-amino-1-hydroxybutylidene-1,1-bisphosphonic acid besides other phosphonic acids. However, high amounts of yellow-orange solid containing monophosphoric acid, phosphorous acid and different phosphonic acids, which is sticky, non-stirrable is generated. Hence, the process in not convenient for industrial scale production. Further, in the '761 patent chlorobenzene is used as the reaction medium, which is harmful, an irritant for skin, eyes and environmentally hazardous.

U.S. Pat. No. 4,705,651 teaches a similar procedure with different molar ratios, which is still not very attractive for industrial scale up.

U.S. Pat. Nos. 4,922,007 and 5,019,651 teach the use of methanesulfonic acid for solubilizing the reaction components. Methanesulfonic acid is expensive, corrosive and irritant. The reaction between methanesulfonic acid and $PCl_3$ is exothermic, which could pose problems in commercial scale operations. Also, large quantity of alkali would be required in the work up for neutralization.

U.S. Pat. No. 5,908,959 teaches use of long chain glycols to attempt to prevent the solidification of the reaction mixture, however the solidification cannot be totally avoided and these glycols cannot be recycled as they get converted to their corresponding chloride derivatives, which could be potentially toxic.

The PCT application WO 02/090367 teaches use of aralkyl or alkyl ethoxylates or triglycerides such as plant or animal oils for solubilization of the reaction mixture.

U.S. Patent Application No. 2003/0013918 teaches the use of an amine hydrochloride in preparation of bisphosphonates from the reaction of a carbonyl compound with a phosphorous halide. This process involves use of concentrated hydrochloric acid as a reactant.

U.S Patent Application No. 2004/0043967 discloses use of aromatic hydrocarbon or a silicone fluid as a diluent for preparation of bisphosphonic acids.

The present invention provides a process wherein a water miscible neutral solvent such as sulfolane is used for preparation of bisphosphonic acid compounds, making the process safe and convenient. We have also found that water miscible neutral ether solvent such as 1,2-dimethoxyethane, 1,4-dioxane, glymes such as diglyme and the like can also be used for preparation of bisphosphonic acids, however sulfolane was observed to provide superior yields. The process of the present invention is suitable for industrial scale up and can be used commercially. Since sulfolane is water miscible and neutral, the reaction mixture can be conveniently worked up by quenching into water, the intermediates subsequently hydrolyzed and the final bisphosphonic acid product directly isolated from the reaction mixture, if desired in the form of a salt thereof.

SUMMARY OF THE PRESENT INVENTION

A process for preparation of bisphosphonic acid, a compound of formula 1 or a salt thereof,

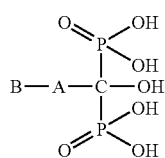

Formula 1 comprising reacting a carboxylic acid compound of formula 2 or a salt thereof

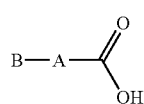

Formula 2 wherein,

A is a straight chain alkyl, a branched alkyl or a cyclic alkyl chain with up to 10 carbon atoms, which can optionally contain hetero atoms in between and, B is alky, aralkyl, aromatic or heteroaromatic group, which can be optionally substituted;

or

wherein, $R_1$ and $R_2$ may be selected from hydrogen or straight chain, branched or cyclic lower alkyl, with phosphorous acid and a phosphorous chloride selected from $PCl_3$, $PCl_5$ and $POCl_3$, in sulfolane.

In first aspect the present invention provides a process comprising reacting 4-aminobutyric acid with phosphorous acid and a phosphorous chloride selected from $PCl_3$, $PCl_5$ and $POCl_3$, in sulfolane to prepare alendronic acid.

In second aspect the present invention provides a process comprising reacting 3-aminopropionic acid with phosphorous acid and a phosphorous chloride selected from $PCl_3$, $PCl_5$ and $POCl_3$, in sulfolane to prepare pamidronic acid.

In third aspect the present invention provides a process comprising reacting 3-pyridylacetic acid with phosphorous acid and a phosphorous chloride selected from $PCl_3$, $PCl_5$ and $POCl_3$, in sulfolane to prepare risedronic acid.

In fourth aspect the present invention provides a process comprising reacting 1-imidazolylacetic acid with phosphorous acid and a phosphorous chloride selected from $PCl_3$, $PCl_5$ and $POCl_3$, in sulfolane to prepare zoledronic acid.

In fifth aspect the present invention provides a process comprising reacting N-(n-pentyl)-N-methyl-3-aminopropionic acid with phosphorous acid and a phosphorous chloride selected from $PCl_3$, $PCl_5$ and $POCl_3$, in sulfolane to prepare ibandronic acid.

In sixth aspect the present invention provides a process comprising reacting 2-(imidazo[1,2-a]pyridin-2-yl)ethanoic acid with phosphorous acid and a phosphorous chloride selected from $PCl_3$, $PCl_5$ and $POCl_3$, in sulfolane to prepare minodronic acid.

In seventh aspect the present invention provides a process comprising reacting 6-aminohexanoic acid with phosphorous acid and a phosphorous chloride selected from $PCl_3$, $PCl_5$ and $POCl_3$, in sulfolane to prepare neridronic acid.

In eighth aspect the present invention provides a process comprising reacting 3-(dimethylamino)propionic acid with phosphorous acid and a phosphorous chloride selected from $PCl_3$, $PCl_5$ and $POCl_3$, in sulfolane to prepare olpadronic acid.

DETAILED DESCRIPTION OF INVENTION

The process of the present invention is characterized by preparation of bisphosphonic acid, a compound of formula 1 or a salt thereof by reacting a carboxylic acid compound of formula 2 or a salt thereof with phosphorous acid and a halophosphorous compound in a water miscible and neutral solvent like sulfolane.

The moiety A is a straight chain, a branched alkyl chain or a cyclic alkyl chain with up to 10 carbon atoms, which can optionally contain hetero atoms in between for e.g., oxygen and sulphur.

The moiety B may be an alkyl, aralkyl, aromatic or heteroaromatic group, that may be monocyclic or polycyclic for example, methyl, ethyl, isopropyl, benzyl, phenyl, pyridinyl, imidazolyl, indolyl, imidazopyridinyl and the like, that may be unsubstituted or substituted.

The substituents $R_1$ and $R_2$ both may be same or different and selected from hydrogen or straight chain, branched or cyclic lower alkyl. The lower alkyl are containing up to 5 carbon atoms for e.g. methyl, ethyl, isopropyl, cyclopropyl.

In the process of the present invention, the preferred halophosphorous compound is a phosphorous chloride e.g. $PCl_3$. $PBr_3$, $POBr_3$ or $PBr_5$ can also be used. The carboxylic acid compound of formula 2 or a salt thereof for example, hydrochloride salt can be used.

The bisphosphonic acids can be obtained in a safe manner, in high yield and purity when using the process of the invention. The present invention uses sulfolane, which is relatively safe and inexpensive, water miscible neutral solvent for preparation of bisphosphonic acids. The hydrolysis of the formed phosphorous intermediates can be carried out in same reaction mixture, and if desired, the pH can be adjusted suitably, for example to about 4.3 and the sodium salt of the bisphosphonic acid can be directly obtained in pure form. It is observed that the process of the present invention provides compounds of formulae 4, 5 and 6 in improved yield and quality.

The compound of formula 2 and the phosphorous acid in sulfolane are reacted with phosphorous trichloride at a suitable temperature, for example, between about 35° C. to about 150° C., preferably at about 60 to about 70° C., at which temperature the phosphonylation reaction is completed in about 3 hours.

The reaction preferably is carried out by combining the carboxylic acid compound with phosphorous acid in presence of sulfolane at a temperature between about 70° C. and about 80° C. for a time between about 1 to about 2 hours. To the reaction mixture at temperature of about 35° C. to about 40° C., the halophosphorous compound like phosphorous chloride is added in small portions. The reaction mixture is heated to a temperature between about 60° C. to about 70° C., preferably about 65° C. to about 67° C. for a period of about 2 to about 4 hours. The reaction mixture containing white solid is cooled to about 0° C. to about 5° C. Then water is added carefully to the reaction mixture to get a clear solution, which is heated to about 100° C. for a period of about 3 to about 4 hours. Thereafter the product bisphosphonic acid can be isolated from the reaction mixture by any means known in the art. For example, the product may be precipitated by cooling to about 0° C. or by combining with a solvent like acetone and isolated by filtration, centrifugation etc.

If it is desired to isolate the bisphosphonic acid as a sodium salt thereof, then after heating the clear solution to about 100° C. for a period of about 3 to about 4 hours as described above, the solution may be cooled to about 0° C. to about 5° C. and thereafter the pH is suitably adjusted with a base like aqueous NaOH and the precipitated salt may be isolated by a manner known in the art. Alternatively, the bisphosphonic acid is suspended in water, pH is suitably adjusted with a base like aqueous alkali or alkaline metal carbonates and the precipitated salt may be isolated by methods known in the art.

In the process of the present invention when:
4-aminobutyric acid is used, the product bisphosphonic acid is alendronic acid,
3-aminopropionic acid is used, the product bisphosphonic acid is pamidronic acid,
3-pyridylacetic acid, a compound of formula 11 is used, the product bisphosphonic acid is risedronic acid,
1-imidazolylacetic acid, a compound of formula 12 is used, the product bisphosphonic acid is zoledronic acid,
N-(n-pentyl)-N-methyl-3-aminopropionic acid is used, the product bisphosphonic acid is ibandronic acid,
2-(imidazo[1,2-a]pyridin-2-yl)ethanoic acid is used, the product bisphosphonic acid is minodronic acid,
6-aminohexanoic acid is used, the product bisphosphonic acid is neridronic acid,
3-(dimethylamino)propionic acid is used the product bisphosphonic acid is, olpadronic acid.

In one embodiment the present invention provides a process for preparation of 4-amino-1-hydroxybutylidene-1,1-bisphosphonic acid (alendronic acid), a compound of formula 3 or salt thereof by reacting 4-aminobutyric acid with phosphorous acid and $PCl_3$ in sulfolane.

In a preferred embodiment alendronic acid monosodium trihydrate is prepared by a process comprising the steps of:
a) reacting 4-aminobutyric acid, phosphorous acid and phosphorous chloride in sulfolane at a temperature of about 60° C. to about 70° C.
b) quenching the reaction mixture with water
c) heating the reaction mixture to about 100° C.
d) cooling and adjusting the pH to about 4.3
e) isolating alendronic acid monosodium trihydrate from the reaction mixture.

In second embodiment the present invention provides a process for preparation of 3-amino-1-hydroxypropylidene-1,1-bisphosphonic acid (pamidronic acid), a compound of formula 4 or salt thereof by reacting 3-aminopropionic acid with phosphorous acid and $PCl_3$ in sulfolane. The resultant pamidronic acid can be in-situ converted to disodium salt thereof or isolated and converted to disodium salt thereof.

In a preferred embodiment pamidronic acid disodium pentahydrate is prepared by a process comprising the steps of:
a) reacting 3-aminopropionic acid, phosphorous acid and phosphorous chloride in sulfolane at a temperature of about 60° C. to about 70° C.
a) quenching the reaction mixture with water
b) heating the reaction mixture to about 100° C.
c) isolating pamidronic acid from the reaction mixture,
d) suspending pamidronic acid in water and adjusting the pH to about 8.0
e) isolating pamidronic acid disodium pentahydrate.

In third embodiment the present invention provides a process for preparation of 1-hydroxy-2-(3-pyridinyl)ethylidene-1,1-bisphosphonic acid (risedronic acid), a compound of formula 5 or salt thereof by reacting 3-pyridylacetic acid,

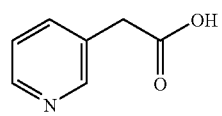

Formula 11 a compound of formula 11 with phosphorous acid and $PCl_3$ in sulfolane. The resultant risedronic acid can be in-situ converted to monosodium salt thereof or isolated and converted to monosodium salt thereof.

In a preferred embodiment risedronic acid monosodium is prepared by a process comprising the steps of:
a) reacting 3-pyridylacetic acid, phosphorous acid and phosphorous chloride in sulfolane at a temperature of about 60° C. to about 70° C.
b) quenching the reaction mixture with water
c) heating the reaction mixture to about 100° C.
d) isolating risedronic acid from the reaction mixture e) suspending risedronic acid in water and adjusting the pH to about 4.3 f) isolating risedronic acid monosodium from the reaction mixture.

In fourth embodiment the present invention provides a process for preparation of 1-hydroxy-2-(imidazol-1-yl)ethylidene-1,1-bisphosphonic acid (zoledronic acid), a compound of formula 6 or salt thereof by reacting 1-imidazolylacetic acid,

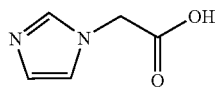

Formula 12 a compound of formula 12 with phosphorous acid and $PCl_3$ in sulfolane.

In a preferred embodiment zoledronic acid monohydrate is prepared by a process comprising the steps of:
 a) reacting 1-imidazolylacetic acid, phosphorous acid and phosphorous chloride in sulfolane at a temperature of about 60° C. to about 70° C.
 b) quenching the reaction mixture with water
 c) heating the reaction mixture to about 100° C.
 d) isolating zoledronic acid monohydrate from the reaction mixture.

The present invention is illustrated by examples and not to be construed as limiting.

EXAMPLES

Example 1

Preparation of Alendronic Acid Monosodium Trihydrate

A suspension of 4-aminobutyric acid (25 g, 0.242 mol) and phosphorous acid (29.8 g, 0.364 mol) in sulfolane (90 ml) was heated to 75° C. for 30 min. The mixture was cooled to 35-40° C. and then gradually introduced phosphorous trichloride (72 ml, 0.824 mol) while maintaining the temperature between 35-45° C. The mixture was heated to 63-67° C. for 3 hours whereby a thick white mass resulted. It was then cooled to 0-5° C. and quenched by slow addition of water (250 ml) over a period of 1 hr. The resulting clear solution is heated at 100° C. for 3 hrs, cooled to ambient temperature and charcoalized. To the charcoalized solution is added 45% w/w sodium hydroxide solution at 0-5° C. until pH is 4.3. The mixture is then stirred for 3 hrs at 0-5° C. and the crystallized product is filtered, washed sequentially with chilled water (100 ml), rectified spirit (75 ml) and dried in air oven at 55-60° C. until water content is between. 16-18% w/w. Yield 54 g, (68.5%), appearance: white crystalline solid, purity >99.0%.

Example 2

Preparation of Pamidronic Acid

A suspension of 3-aminopropionic acid (25 g, 0.280 mol) and phosphorous acid (34.5 g, 0.421 mol) in sulfolane (90 ml) is heated to 75° C. for 30 min. The mixture is cooled to 35-40° C. and then gradually introduced phosphorous trichloride (83 ml, 0.954 mol) while maintaining the temperature at 35-45° C. The mixture is heated to 63-67° C. for 3 hrs, whereby white solid results. It is then cooled to 0-5° C. and quenched by slow addition of water (250 ml) at 0-5° C. over a period of 1 hr. The resulting clear solution is charcoalized and is heated at 100° C. for 3 hrs, cooled to ambient temperature. Cooled the charcoalized solution and stirred for 4 hrs at 0-5° C. The crystallized product is filtered, washed sequentially with chilled water (100 ml), rectified spirit (75 ml) and dried in air oven at 55-60° C. until water content is less than 0.5% w/w. Yield 41.4 g, (62.7%), appearance: white crystalline solid, purity >99.0%.

Example 3

Preparation of Pamidronic Acid Disodium Pentahydrate

To a stirred suspension of pamidronic acid (25 g) in water (200 ml) is added 20% w/w sodium hydroxide solution at 20-25° C. until pH is 8.0. The resulting mixture is stirred for 4 hours at 20-25° C. and then for 1 hour at 2-5° C. The crystallized product is filtered, washed with chilled water (50 nm) and dried in air oven at 55-60° C. until water content is between. 23-27% w/w. Yield 30 g, (76.4%), appearance: white crystalline solid, purity >99.0%.

Example 4

Preparation of Risedronic Acid

A suspension of 3-pyridylacetic acid hydrochloride (50 g, 0.288 mol) and phosphorous acid (35.4 g, 0.432 mol) in sulfolane (180 ml) is heated to 75° C. for 30 min. The mixture is cooled to 35-40° C. and then gradually introduced phosphorous trichloride (85.6 ml, 0.98 mol) while maintaining the temperature between 35-45° C. The mixture is heated to 63-67° C. for 3 hours whereby a thick white mass results. It is then cooled to 0-5° C. and quenched by slow addition of water (500 ml) at 0-5° C. over a period of 1 hour. The resulting clear solution is charcoalized and heated at 100° C. for 3 hrs, cooled to ambient temperature and then cooled 0-5° C. After stirring for 2 hrs at 0-5° C. the crystallized product is filtered, washed sequentially with chilled water (100 ml), rectified spirit (75 ml) and dried in air oven at 55-60° C. until loss on drying is less than 0.5% w/w. Yield 60.4 g, (70.47%), appearance: white crystalline solid, purity >99.0%.

Example 5

Preparation of Risedronic Acid Monosodium

To a stirred suspension of risedronic acid (25 g) in water (200 ml) is added 20% w/w sodium hydroxide solution at 0-5° C. until pH is 4.3. The resulting mixture is stirred for 2 hrs at 0-5° C. The crystallized product is filtered, washed sequentially with chilled water (50 ml) and rectified spirit (50 ml), dried in air oven at 55-60° C. until loss on drying is between. 13.5-16.5% w/w. Yield 30 g, (76.4%), appearance; white crystalline solid, purity >99.0%.

Example 6

Preparation of Zoledronic Acid Monohydrate

A suspension of 1-imidazolylacetic acid (50 g, 0.396 mol) and phosphorous acid (48.7 g, 0.594 mol) in sulfolane (180 ml) is heated to 75° C. for 30 min. The mixture is cooled to 35-40° C. and then gradually introduced phosphorous trichloride (117 ml, 1.346 mol) while maintaining the temperature between 35-45° C. The mixture is heated to 63-67° C. for 3 hrs, whereby white solid results. It is then cooled to 0-5° C. and quenched by slow addition of water (500 ml) at 0-5° C. over a period of 1 hr. The resulting clear solution is heated at 100° C. for 3 hrs, cooled to ambient temperature and charcoalized. To the charcoalized solution is added acetone (800 ml). The mixture is then stirred for 4 hrs at 20-25° C. and the crystallized product is filtered, washed sequentially with chilled water (200 ml), acetone (100 ml) and dried in air oven at 55-60° C. until water content is between. 6.2-7.2% w/w. Yield 81.3 g, (70.7%), appearance: white crystalline solid.

Example 7

Preparation of Zoledronic Acid Monohydrate

A suspension of 1-imidazolylacetic acid (20 g, 0.159 mol) and phosphorous acid (19.6 g, 0.239 mol) in 1,2-dimethoxyethane (72 ml) is heated to 75° C. for 30 minutes. The mixture is cooled to 35-40° C. and then gradually introduced phosphorous trichloride (48 ml, 0.543 mol) while maintaining the temperature between 35-45° C. The mixture is heated to 63-67° C. for 3 hrs, whereby white solid results. It is then cooled to 0-5° C. and quenched by slow addition of water (160 ml) at 0-5° C. over a period of 1 hr. The resulting clear solution is heated at 100° C. for 3 hrs, cooled to ambient temperature and charcoalized. To the charcoalized solution is added acetone (320 ml). The mixture is then stirred for 4 hours at 20-25° C., the crystallized product is filtered, washed sequentially with chilled water (80 ml), acetone (80 ml) and dried in air oven at 55-60° C. until water content is between 6.2-7.2% w/w. Appearance: white crystalline solid, purity >99.5%, meeting specification as per IHS.

The invention claimed is:

1. A process for preparation of bisphosphonic acid, a compound of formula 1 or a salt thereof,

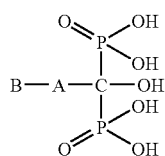

Formula 1 comprising reacting a carboxylic acid compound of formula 2 or a salt thereof

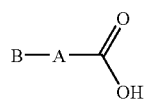

Formula 2 wherein,

A is a straight chain alkyl, a branched alkyl or a cyclic alkyl chain with up to 10 carbon atoms, which can optionally contain hetero atoms in between and, B is alkyl, aralkyl, aromatic or heteroaromatic group, which can be optionally substituted;

or

wherein, $R_1$ and $R_2$ may be selected from hydrogen or straight chain, branched or cyclic lower alkyl, with phosphorous acid and a phosphorous chloride selected from $PCl_3$, $PCl_5$ and $POCl_3$, in sulfolane.

2. The process as claimed in claim 1, wherein the carboxylic acid is 4-aminobutyric acid and the bisphosphonic acid is alendronic acid.

3. The process as claimed in claim 1, wherein the carboxylic acid is 3-aminopropionic acid and the bisphosphonic acid is pamidronic acid.

4. The process as claimed in claim 1, wherein the carboxylic acid is 3-pyridylacetic acid and the bisphosphonic acid is risedronic acid.

5. The process as claimed in claim 1, wherein the carboxylic acid is 1-imidazolylacetic acid and the bisphosphonic acid is zoledronic acid.

6. The process as claimed in claim 1, wherein the carboxylic acid is N-(n-pentyl)-N-methyl-3-aminopropionic acid and the bisphosphonic acid is ibandronic acid.

7. The process as claimed in claim 1, wherein the carboxylic acid is 2-(imidazo[1,2-a]pyridin-2-yl)ethanoic acid and the bisphosphonic acid is minodronic acid.

8. The process as claimed in claim 1, wherein the carboxylic acid is 6-aminohexanoic acid and the bisphosphonic acid is neridronic acid.

9. The process as claimed in claim 1, wherein the carboxylic acid is 3-(dimethylamino)propionic acid and the bisphosphonic acid is olpadronic acid.

10. The process as claimed in claim 2, wherein the yield of alendronic acid is 69% of theoretical yield and the purity of the alendronic acid is at least 99%.

11. The process as claimed in claim 3, wherein the yield of pamidronic acid is 76% of theoretical yield and the purity of the pamidronic acid is at least 99%.

12. The process as claimed in claim 4, wherein the yield of risedronic acid is 70% of theoretical yield and the purity of the risedronic acid is at least 99%.

13. The process as claimed in claim 5, wherein the yield of zoledronic acid is at least about 70% of theoretical yield.

14. The process as claimed in claim 5, wherein the purity of the zoledronic acid is at least 99.5%.

* * * * *